United States Patent [19]
Roper

[11] Patent Number: 4,757,024
[45] Date of Patent: Jul. 12, 1988

[54] IMMUNE COMPLEX DETECTION METHOD AND ARTICLE USING IMMUNOLOGICALLY NON-SPECIFIC IMMUNOGLOBULINS

[75] Inventor: Michael D. Roper, Lafayette, Colo.

[73] Assignee: Biostar Medical Products, Inc., Boulder, Colo.

[21] Appl. No.: 763,955

[22] Filed: Aug. 8, 1985

Related U.S. Application Data

[63] Continuation-in-part of Ser. No. 740,018, May 31, 1985, abandoned.

[51] Int. Cl.4 ................. G01N 33/564; G01N 33/544
[52] U.S. Cl. .................................... 436/507; 530/412; 530/413; 530/811; 530/812; 435/7; 435/177; 435/803; 436/508; 436/509; 436/518; 436/528; 436/536; 436/538; 436/541; 436/809; 436/811; 436/824
[58] Field of Search .................. 424/16; 422/57, 58; 435/4, 7, 177, 803; 530/811, 812, 412, 413; 436/536, 538, 541, 506, 507, 508, 509, 518, 528, 821, 824, 811, 809

[56] References Cited

U.S. PATENT DOCUMENTS

| 4,233,286 | 11/1980 | Soothill et al. | 436/507 |
| 4,307,190 | 12/1981 | Masson et al. | 436/821 |
| 4,329,331 | 5/1982 | Kallick | 436/506 |
| 4,332,783 | 6/1982 | Pernice et al. | 436/506 |

OTHER PUBLICATIONS

Jones et al., J. of Immunological Methods, vol. 44, (1981), 249–270.

Primary Examiner—Christine M. Nucker

[57] ABSTRACT

The use of immunologically non-specific peptide linked amino acids containing compounds that are capable of immobilizing circulating immune complexes for the purpose of detection or removal from serum or blood, such compounds including oligopeptides, modified oligopeptides, polypeptides, modified polypeptides, proteins, modified proteins, and in particular glycosylated polypeptides and proteins.

6 Claims, 7 Drawing Sheets

REMOVAL OF IMMUNE COMPLEXES FROM SERUM, PLASMA, & WHOLE BLOOD USING COLUMNS OF GLYCOPROTEIN-COATED POLYSTYRENE BEADS.

IMMUNE COMPLEX DETECTION METHOD AND ARTICLE USING IMMUNOLOGICALLY NON-SPECIFIC IMMUNOGLOBULINS

BACKGROUND OF THE INVENTION

This is a Continuation-In-Part of U.S. patent application Ser. No. 740,018, filed May 31, 1985, now abandoned.

The immune system represents the body's major defense mechanism against infective agents. There are two functional divisions of the vertebrate immune system; humoral and cell mediated. Humoral immunity represents circulating components of the immune system which are produced by cells and secreted, thus may be found in serum. Cell-mediated immunity is conferred through the direct action of various leukocytic cells upon the targeted foreign substance. Concerted action of these two interrelated systems affords protection from a wide variety of infectious diseases.

Under normal circumstances, bodily invasion by infectious agents provokes a response from the cells which make components of the humoral system. Specifically, B lymphocytes synthesize specific proteins, that is, antibodies, which bind to selected sites on the invading organism. After the antibodies bind to the invading organisms, the invading organisms may then be destroyed through action of the cell-mediated immune system, or action of humoral fractions, or directly inactivated by the antibody molecules themselves.

Ordinarily, antibody molecules are not directed at the host's own or "self" agents. In certain individuals, however, the immune system mistakes self components for foreign invaders. When this occurs, the body mounts an immune attack against itself, much in the same manner that it would for a foreign invader. The results of such an autoimmune conflict are dramatic. Symptoms of such diseases include the inability to utilize sugar (type I diabetes), destruction of joints (rheumatoid arthritis), kidney destruction (systemic lupus erythematosus, glomerulonephritis, and like diseases), and destruction of the vascular system (vasculitis). Each autoimmune disorder leads to prolonged suffering together with elevated mortality rates.

Autoimmune diseases are accompanied by persistently high concentrations of blood-borne autoimmune complexes. Much of the damage wrought by the autoimmune disease may be traced to the efforts of the cell-mediated immune system to eliminate those autoimmune complexes, wherever they may be found. Control of these diseases has proven difficult in the past partly because the detection methods employed inadequately discriminated between levels of immune complexes that reflected either normal or disease status.

Many different techniques have been tried in search of accurate, rapid, and inexpensive methods of immune complex detection for disease states characterized by immune complex formation, including autoimmune diseases. Although often quite ingenious, no method has proven to be totally adequate. Examples of the limitations in the prior methods of detection follow.

Firstly, the Raji cell assay depends upon the presence of cell surface receptors for immune complexes, and these receptors only appear at precise times in the growth of the culture.

Secondly, complement fractions or antibodies directed against them are often employed in radioimmuno or enzyme-linked immunosorbant assays. Unfortunately, both complement and antibody used to immobilize the complement are labile proteins. This instability leads to loss of sensitivity, specificity and reproducibility. Consequently, methods which depend upon complement immobilization either by direct or antibody-mediated adherence, are not sufficiently reliable for clinical testing because of this labile property.

Thirdly, immunoglobulin class and size limit the utility of complement-based assays. Neither Raji cell nor complement-based assays can detect all classes and subclasses of antibodies in the immune complex; they are restricted to IgM, $IgG_1$, $IgG_2$, and $IgG_3$. Raji cell and other complement-based methods also can only detect complexes with molecular mass greater than 1,000,000 Daltons. These two criteria are the most limiting for Raji cell and complement-based assay systems.

Lastly, liquid physicochemical techniques utilizing precipitation with substances like polyethylene glycol, dextran, or *Staphylococcus aureas* protein A are unwieldly because of the difficulties inherent to handling small and often flocculent precipitates. Also, adventitious binding of immunologically unrelated immunoglobulins to the precipitate further degrades the performance of such tests. These difficulties combine to hamper the utility of these methods of immune complex measurement. To overcome these limitations, numerous tests must be run, thereby increasing the cost to the patient. As a consequence, the various tests are not normally performed at sufficient frequency to properly monitor the progress of a patient's disease. Development of an inexpensive selective, effective means of adhering the immune complex to a solid support is essential to surmount these problems.

It is therefore an objective of the present invention to provide compositions, methods and articles for the selective adsorption or affixing of immune complexes which will be effective for detecting a wide variety of classes and subclasses of immune complexes. It is a further objective of this invention to overcome the aforementioned selectivity, stability, and handling disadvantages inherent in all other methods of immune complex adsorption to solid surfaces for the purposes of assay, removal of immune complexes from serum, and the like. It is furthermore an objective of this invention to provide novel, highly adaptable, and readily utilizable means for detection of components of said complexes after affixation to a support, and further to use such techniques for the purposes of clinical detection, removal, concentration, or any other purpose associated with human or veterinary medical applications.

BRIEF SUMMARY OF THE INVENTION

The present invention includes novel compositions, novel methods and articles for the direct selective absorption, adsorption or attachment, by whatever mechanism, of immune complexes from serum or other body fluids, for the purpose of identification, quantitation or removal. The present invention utilizes, in its broadest sense, immunologically non-specific peptide linked amino acids, which have a particular affinity for attaching immune complexes. As described herein, the immunologically non-specific peptide linked amino acids and similar modified peptide linked amino acids are employed to directly and selectively affix immune complexes from serum or other body fluids.

The immunologically non-specific peptide linked amino acids which can be employed advantageously in the practice of the present invention include oligopeptides, polypeptides, and proteins as well as modified or substituted oligopeptides, polypeptides and proteins. Preferably, polypeptides and proteins that are glycosylated or modified with functionally equivalent substituents, such as thiosugars, hydroxy or thioamino acids, hydroxy or thiolipids, or chemically related or similar substances, have been found to be capable of directly bonding with immune complexes. More preferably, glycosylated proteins are utilized (hereinafter glycoproteins) and most preferably, certain globulin fractions such as immunologically non-specific gammaglobulins are particularly effective in the practice of the present invention.

Whether the immune complexes comprise any single class or subclass of antibody or whether the fluid containing the immune complexes derives from corporeal or extracorporeal origin, does not appear to be limiting to the utility of the present invention, as physicochemical alterations to the antibodies, after binding to antigens render them selectively susceptible to immobilization.

The source of the glycoproteins selected for use herein is a particular purified gammaglobulin fraction (Cohn, E. J. (1946), J. American Chemical Society 68, 459). These glycoproteins were derived from animals not immunized against human proteins or immune complexes derived therefrom; hence, these agents do not appear to affix immune complexes through any immune "Fab"-determinant reaction. Instead, on the basis of the evidence observed, they appear to affix complexes through interaction of the carbohydrate moiety found chiefly in the "Fc" portion of the antibody molecule. In this way, the present invention is quite different than prior methods describing proteinaceous fixation of immune complexes.

While such glycoprotein preparations have long been used to prevent adventitious adherence of free antibodies to solid supports, it is unique and highly surprising to find that a coating of glycoproteins on a solid support selectively affixes antibodies which are immunologically bound to antigens. Thus, a coating of gammaglobulins demonstrates both desorption for free antibodies and adsorption for immune complexes. The present invention now provides a way to substantially improve detection methods for immune complexes in serum and in the blood and other body fluids. It also provides a particularly useful method for selective removal of such complexes from the blood of those suffering from autoimmune and other diseases characterized by the formation of immune complexes.

According to the preferred practice of this invention, a film of glycoproteins, selected from the group described herein, is first affixed to a solid support medium to serve as a selective adsorbant for affixing any immune complex as might be present in the fluid to be contacted with the film. The glycoprotein coat may be any possessing the described ability to affix the immune complex, an immunologically non-specific bovine gammaglobulin fraction obtained as described, being preferred.

After affixing the described coating to the solid support medium, the glycoprotein coated support can then selectively adsorb immune complexes from any fluid containing immune complexes which is contacted with the coating. The affixed immune complexes may then be either: (1) assayed for any of their components, with any immunoassay method, the enzyme-linked immunosorption assay method being preferred; or (2) concentrated and purified; or (3) the fluid may be returned to the patient without the removed immune complexes if desired for a clinical therapeutic utility.

In the following examples the described film is formed by exposing the selected gammaglobulin fraction to pH-dependent denaturation; however, any form of fixation of the selected glycoprotein is suitable so long as the ability of the film to specifically and selectively affix immune complexes is retained. Such examples of fixation include, but are not limited to, thermal aggregation, chaotropic unfolding, crosslinking with chemical agents, such as glutaraldehyde, drying, freezing, and the like methods.

Subsequent qualitative and quantitative detection of the complex is thereby made relatively easy since enzyme-conjugated antibodies specific for any immunoglobulin class are readily available. The actual visual or machine readable quantitation of the immune complexes adhering to the support is accomplished by the use of the ELISA techniques first described by Engvall and Perlman ((1971) Immunochemistry 8, 871–874 and (1972) J. Immunology 109, 129–135), and The Enzyme Linked Immunosorbent Assay (ELISA) by Voller, A., Bidwell, D. E. and Bartlett, A., (1979) Dynatech Laboratories, Inc., Alexandria, Va., both of which are, in their totality, incorporated herein by reference. It is also possible to detect the presence of specific complex-bound antigens through the use of enzyme conjugated antibodies directed against that antigen.

DETAILED DESCRIPTION OF THE INVENTION

Figure 1:
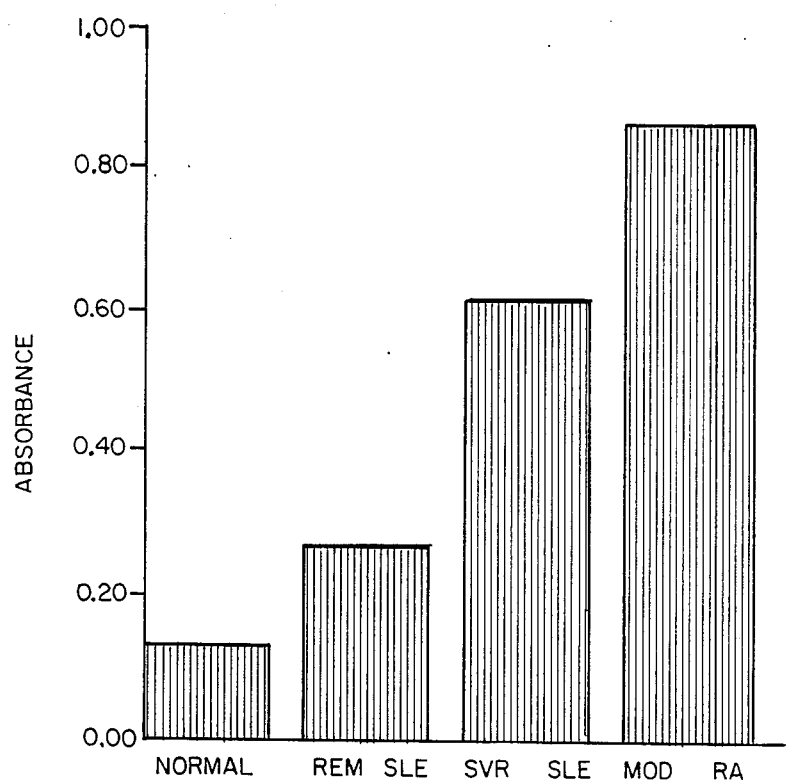
FIG. 1 is a bar graph of absorbance values for specific immunoassays of normal and disease states run according to the present invention.

The following definitions are supplied for the purposes of clarifying aspects of this invention:

Immunologically non-specific peptide linked amino acids: As used herein, this means oligopeptides, polypeptides and proteins as well as modified oligopeptides, polypeptides and proteins, which are derived from organisms which have not been immunized against any antigenic determinant derived from any part of the animal specie being tested or otherwise associated with such specie, or immune complexes derived therefrom and have the functional ability to attach to, adhere, affix, or otherwise immobilize in situ, immune complexes present in such specie. In addition to the foregoing naturally occurring substances, this definition also includes peptide-linked amino acids which are created synthetically. Such synthesis can be accomplished in a peptide synthesizer or through similar chemical processes, or produced by genetic alteration of existing or newly created viruses, bacteria, fungi, yeast or other recombinant, or hybrid cell vectors or hosts. It is therefore contemplated that the defined oligopeptides, polypeptides and proteins, and modified oligopeptides, polypeptides and proteins, derived from one specie that has not been immunized against another specie, or synthesized as described should be useful in the practice of the present invention if they exhibit the ability to attach to, adhere, affix or otherwise immobilize, in situ, immune complexes present in the tested specie.

Glycoprotein: As used herein, is intended to mean any combination of polysaccharide and protein or polypeptide from an immunologically naive or immunologically non-specific peptide linked amino acid for which the two agents are attached through covalent bonds between the polysaccharide and protein/polypeptide.

Gammaglobulin: Any member of globular glycoproteins having electrophoretic mobility in the "gamma" region of serum proteins subjected to the procedure.

Immunoglobulin: Any member of the gammaglobulin fraction possessing chemical ability to bind to another agent, such agents including proteins, carbohydrates, nucleic acids, complex lipids, simple organic compounds, or any other compound interacting with the immunoglobulin through topographically determined binding at the "Fab" region.

Antibody: A member of the Immunoglobulin class of proteins. Mammalian antibody molecules comprise at least two Fab and one Fc region in their structures.

Antigen: Any compound against which antibody molecules may be directed provided binding occurs to the antibody at the binding site found in the Fab portion of the antibody molecule.

Immunoglobulin Classes: Immune globulins separated according to electrophoretic mobility. Recognized classes of immunoglobulins include but are not limited to immunoglobulins A, D, E, G, and M. These classes are abbreviated IgA, IgD, IgE, IgG, and IgM respectively.

Immune complex: Any combination of antibodies and antigens in which the binding occurs through interaction between Fab sites on the antibody and topographic features of the antigen.

Immune Response: Any response of a particular immune system during which specific antigens act to cause the formation of antibodies directed against the antigen or to cause the specific activation of cellular defense mechanisms resulting in antigen engulfment, cytotoxic response, or other action by cells or the cell-mediated system.

Immunologically Naive: The condition of the immune system in an animal or group of animals, including human beings, which have never been exposed to an antigen in such a manner as to produce a product of an immune response, either humoral or cell mediated.

Complement: The thermolabile substance, normally present in serum, that is destructive to certain bacteria and other cells sensitized by a specific complement-fixing antibody.

Serum: Is intended to mean the fluidic component of any bodily fluid remaining after cells and coagulable proteins such as fibrin which may be present in such bodily fluidic components have been removed by appropriate physical, chemical, or physicochemical means. Typically, this term refers to the residual watery fluid remaining after clotting of blood and removal of the clot, but in its broad sense is intended to include the fluidic component of cerebrospinal fluid, urine, interstitial fluid, cellular cytoplasm, and the like.

Alkaline carbonate buffer: Unless otherwise specified is intended to mean a solution prepared to be the equivalent of one-tenth mole of sodium bicarbonate dissolved in 900 ml of demineralized water. The pH was adjusted to 9.6 with sodium hydroxide, and the volume of the solution was adjusted to one liter by the addition of demineralized water.

Bovine gammaglobulin solution: Purified bovine gammaglobulins (Cohn, E. J. (1946) J. American Chemical Soc. 68, 459) were dissolved in alkaline carbonate buffer at the extent of 1.0 mg bovine gammaglobulins/ml of solution.

Phosphate buffered saline: Sodium chloride was added to water to the final concentration of 9 g/l. To this solution was added 0.01 moles of potassium phosphate (monobasic). The pH was adjusted to 7.4 and the solution volume brought to exactly 1.00 liter by the addition of demineralized water.

Tween-20: A polyoxyethylene sorbitan monolaureate: In the description, this compound was added to phosphate buffered saline for some steps. When indicated, Tween-20 was used at a concentration of 0.05% (v/v). Nonionic detergents such as Tween-20 are used to prohibit adventitious binding of proteins.

Conjugated antibodies: For the enzyme immunoassay portion of the determination, antibodies directed against human immunoglobulin fractions were obtained. These antibodies had been chemically conjugated with horseradish peroxidase to serve as a detection agent. Said antibody preparations were diluted between 500 and 2000 fold in phosphate-buffered saline containing Tween prior to use.

Substrate solution: To quantitate the horseradish peroxidase, a solution of orthophenylene diamine (400 $\mu$g/ml) was prepared together with 10 $\mu$M hydrogen peroxide in phosphate buffered saline. The solution was prepared just before use, and stored in the dark to prevent photolytic decomposition.

Labelled Antibodies: Any antibody substance which has been covalently or otherwise combined with a molecule or ion for the purpose of selectively identifying that group of antibodies. Such adduct molecules or ions include enzymes, fluorescent substances, radionuclides, and the like.

Labelled Antigens: Any antigen substance which has been covalently or otherwise combined with a molecule or ion for the purpose of selectively identifying that group of antigens. Such adduct molecules or ions include enzymes, fluorescent substances, radionuclides, and the like.

Optical Density (OD) or Absorbance: A number which refers to the color absorbance of a sample. Optical density is related to the percent of light transmitted through the sample by the following formula:

$$OD = 2 - \log(\text{percent transmittance})$$

Glycoproteins and glycopeptides can be affixed to plastics and other solid supports by denaturation at a predetermined alkaline pH value. As described hereinafter, such glycoproteinaceous films possess the unusual characteristics of selectively adhering immune complexes which may be present in a sample of biological fluids that are placed in contact with the film-coated surface. What follows is a description of a preferred embodiment of the coatings of the present invention, together with the preferred methods for adhering immune complexes, such as may be found in a sample of bodily fluid, including the method for detecting the complexes so bound to the solid support. Gammaglobulins obtained from an animal population not previously challenged with human serum proteins are a preferred embodiment of this method.

Step 1: AFFIXATION OF THE GLYCOPROTEIN COAT. Purified bovine gammaglobulins are contacted with a buffer comprising 0.1 molar sodium bicarbonate, pH 9.6. The final concentration of gammaglobulins in the resultant solution is 1.0 mg/ml (w/v). This solution is used for preparation of the glycoprotein coat.

To affix a thin film of bovine gammaglobulins to a receiving surface, 200 microliters of the previously prepared solution of bovine gammaglobulins is added to each well of a 96 well titer plate, such as a Dynatech Immulon II plate. The plate is placed into a humidified chamber maintained at 37° C. and removed from the chamber after 4 hours.

Unbound bovine gammaglobulin proteins are removed by shaking the solution from the plate, then washing the plate thrice with a 0.9% (w/v) saline solution containing 0.01 molar potassium phosphate, pH 7.4.

Step 2: ADHERING IMMUNE COMPLEXES TO THE PREPARED PLATE PREPARED IN STEP 1. Prior to contacting the bodily fluid with the prepared plate, the fluid is diluted properly by adding aliquots of serum to phosphate buffered saline. Dilution is necessary to yield appropriate amounts of color during step 3, the enzyme linked assay. For most of the following examples, the optimum preferred dilution for this assay is 1:15 (volume serum:volume diluent), although wide latitudes of dilution can be used, depending upon the nature of the bodily fluid subjected to the assay and the assay detection techniques employed. Preparation of the fluid may also include adding immunologically nonspecific peptide linked amino acids (as defined herein) to the fluid.

The diluted sample of bodily fluid is then placed into appropriate wells of the titer plate. Adherence of the immune complexes contained in the samples to the solid support was enhanced by incubation at 37° C. for not less than 10 minutes. In the following assay examples, the adherence incubation described in this paragraph was continued for 30 minutes.

Following incubation to achieve complex adherence, the samples are shaken from the wells together with such noncomplexed antibodies that are present in the sample. This is done since there are many more free antibodies than there are antibodies bound in complexes and residual free antibodies would elevate background absorbance values. The plates are then washed three times with phosphate-buffered saline, as described in Step 1 above. To this buffered medium is also added 0.05% (v/v) Tween-20 to further reduce adventitious binding of the free antibodies.

Step 3: ASSAY FOR IMMUNE COMPLEX AFFIXED TO THE PLATE. Standard enzyme-linked assay techniques, previously described, are used for the assay of immune complexes, although any suitable means of detection such as radioactive labeling, fluorescence, or the like can be employed. For the examples described hereinafter, anti-human IgG induced in goats was used to ascertain whether the complex contained human IgG. These antisera were linked to horseradish peroxidase, an enzyme which yields a colored product whenever one of its substrates is present together with hydrogen peroxide. The substrate should be chosen to be consistent for the enzymic activity added to the antibody. For the examples described hereinafter, the substrate was ortho-phenylene diamine. The product of the reaction catalyzed by horseradish peroxidase under these circumstances is nitroaniline, which has a chestnut brown color in an acid solution.

The enzyme conjugated goat antibody solution, prepared as described, is then added to each of the wells of the titer plate. Binding of these probing antibodies to the human IgG fraction of the complex is permitted for at least 15 minutes at 37° C. The plate is removed from the incubating chamber, emptied of its contents, and washed as in Step 2. The last wash is best performed with Tween-free buffer to avoid inhibition of the attachment of the horseradish peroxidase enzyme.

The presence of a label, as previously described, is determined by incubating the plates with a solution of phosphate-buffered saline containing ortho-phenylamine diamine (400 μg/ml) and 3-10 micromolar hydrogen peroxide at room temperature in the dark. The reaction is permitted to continue for 10 minutes, or until sufficient color appears to be read on the spectrophotometric device used. The reaction is subsequently stopped through the addition of an equal volume of 2.5 molar sulfuric acid, and the intensity of color (the optical density, or OD or absorbance) is read by a spectrophotometric device such as a Dynatech MR600 or the like.

As with any enzyme-linked immune assay, the resultant color of the reaction product is proportional to the number of conjugated antibodies which have bound to the immune complex. For most cases, the number of bound conjugated antibodies is linearly related to the number of human IgG molecules present in the immune complex. Hence, as the amount of immune complex fixed on the film increases, so does the optical density, or absorbance of the enzyme reaction.

EXAMPLES

EXAMPLE 1

Selectivity of Glycoprotein Films for Absorption of Immune Complexes from Serum

A polystyrene plate was coated with a film of bovine gammaglobulins by the following procedure:

(1) Purified bovine gammaglobulins from a Cohn fraction II preparation were dissolved in an alkaline buffer (0.1M sodium carbonate, pH 9.6).

(2) The alkaline solution containing the bovine gammaglobulins was placed in contact with the plate for 4 hours at 37° C.

(3) The coating solution was shaken from the plate, after incubation. The plate was washed three times with a solution of sodium chloride (0.15M), buffered by potassium phosphate (0.01M, pH 7.4) to remove unbound gammaglobulin proteins.

The bovine gammaglobulin-coated plate was then used to determine the presence of immune complexes in human serum samples drawn from individuals with:

(1) no apparent pathology; (NORMAL)

(2) systemic lupus erythematosus in remission (REM SLE);

(3) moderate systemic lupus erythematosus or advanced systemic lupus erythematosus, (SVR SLE); and (4) moderate rheumatoid arthritis (MOD RA).

These sera had been previously shown to contain immune complexes appropriate for their pathological status by Clq ELISA tests and radial immunodiffusion methods.

A representative immune complex assay, as described hereinafter, using the bovine gammaglobulin-coated plates, prepared as previously described, is presented in Table 1, and graphically displayed in FIG. 1. The procedures used to derive these data are summarized below:

(1) Sera were diluted properly with a solution of 0.15M NaCl in 0.01M Sodium Phosphate buffer (pH 7.4) prior to the test (hereinafter denoted PBS). In this example, one volume of serum was diluted with 15 volumes of PBS.

(2) 0.1 ml aliquots of the diluted sera were placed into appropriately designated wells. For this example, 7 replicate determinations were performed on each specimen, and averaged.

(3) The plate containing the specimens was placed into a humidified incubator at 37° C. for 30 minutes. Following incubation, the plate was removed from the incubator, the liquid shaken out, and the plate washed three times with PBS containing 0.5 ml polyoxyethylene sorbitan monolaurate (Tween-20) per liter of solution.

(4) The plate was exposed to a mixture containing horseradish-peroxidase conjugated antibodies specific for human immunoglobulin G. The plates were incubated at 37° C. for 15 minutes to attach the conjugated anti-IgG. After incubation, the plates were washed thrice with PBS to remove the unbound enzyme-conjugated antibodies.

(5) Each well in the plate was assayed for horseradish peroxidase activity by adding PBS containing o-phenylenediamine and hydrogen peroxide. The presence of complexes was thus detected by the intense chestnut-brown color appearing after reaction was terminated with sulfuric acid. The color was quantitated at 490 nm using a Dynatech MR 600 plate reading spectrophotometer. Reagent blanks for spectrophotometric calibration were wells in the plate which were not contacted with human serum.

TABLE 1
ADSORPTION OF IMMUNE COMPLEXES BY GLYCOPROTEIN COATS

| Serum Source | Mean Optical Density (Mean Adsorbance) | Standard Error |
|---|---|---|
| Normal | 0.133 | 0.004 |
| Remission SLE | 0.269 | 0.006 |
| Severe SLE | 0.617 | 0.008 |
| Moderate RA | 0.869 | 0.013 |

Legend:
The numbers listed under MEAN OPTICAL DENSITY (MEAN ADSORBANCE) refer to the optical density read at 490 nm, obtained during the assay described above.
The numbers given are the average of the results of seven assays per sample.
The number under the Standard Error heading refers to the standard error of the mean.
Abbreviations:
SLE: Systemic Lupus Erythematosus
RA: Rheumatoid Arthritis The ability of bovine gammaglobulin-treated support mediums to adsorb immune complexes is demonstrated by the increased absorbance exhibited in wells exposed to serum drawn from individuals diagnosed as suffering from immune complex disease. Furthermore, good correlation was observed between the severity of disease and the amount of color found by the procedure. Normal human serum did not elicit appreciable color in the assay, yielding additional evidence of coated plate specificity for immune complexes. The same procedure has been demonstrated to work equally well for whole blood and anticoagulated plasma.

EXAMPLE 2

Adsorption of Immune Complexes from Serum by Uncoated Polystyrene Plates

Figure 2:
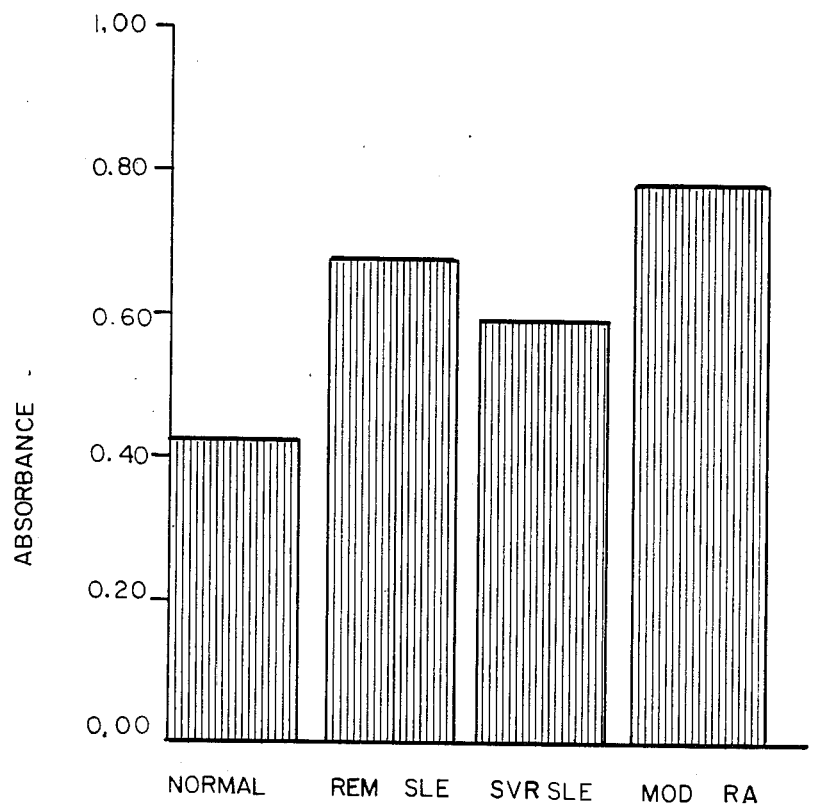
FIG. 2 is a bar graph of absorbance values for specific immunoassays of normal serum and serum containing immune complexes run on uncoated polystyrene plates.

To demonstrate the beneficial effect of glycoprotein coating, a polystyrene plate was left uncoated but was exposed to the sera described in Example 1 under identical incubation conditions. The plate was then exposed to peroxide-conjugated anti-IgG and assayed for peroxidase as before. As expected, only slight selectivity is exhibited by untreated plates. Additionally, very high backgrounds were also observed, unlike the selectivity and backgrounds found for plates precoated with glycoproteins such as bovine gammaglobulins. The results obtained by this manipulation are presented in Table 2 and displayed graphically in FIG. 2. Each bar height shown in FIG. 2 represents the mean absorbance for seven replicate assays.

TABLE 2
ADSORPTION OF IMMUNE COMPLEXES BY UNCOATED POLYSTYRENE

| Serum Source | Mean Optical Density (Mean Adsorbance) | Standard Error |
|---|---|---|
| Normal | 0.431 | 0.020 |
| Remission SLE | 0.682 | 0.021 |
| Severe SLE | 0.599 | 0.041 |
| Moderate RA | 0.781 | 0.031 |

Legend:
As in Table 1, the numbers listed under Optical Density refer to the MEAN OPTICAL DENSITY (MEAN ADSORBANCE) at 490 nm obtained during the assay described above.
The numbers given are the average of the results of seven assays per sample.
The number under the Standard Error heading refers to the standard error of the mean.
Spectrophotometric blanks were performed using uncoated plastic wells not exposed to human serum. Such blanks were treated to all subsequent steps including exposure to conjugated antibodies and assay for peroxidase. No color was apparent in the blankwells.
Abbreviations:
SLE: Systemic Lupus Erythematosus
RA: Rheumatoid Arthritis

EXAMPLE 3

Figure 3:
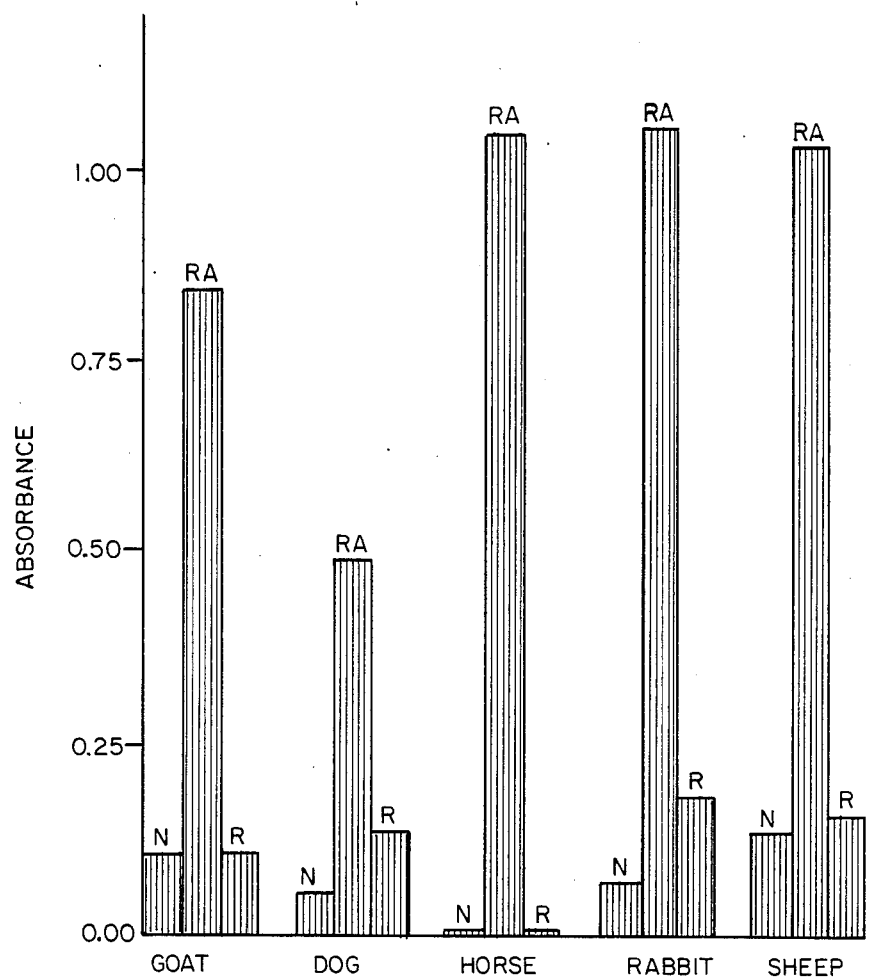
FIG. 3 is a bar graph of absorbance values for specific immunoassays using immunologically non-specific glycoproteins from the sources indicated.

Purified gammaglobulins from a variety of species were used for plate treatment as described in Example 1. The plates were subsequently exposed to immune complex rich or immune complex poor sera as described in Example 1. Following exposure and washing, the plates were assayed for presence of attached immune complexes using horseradish peroxidase-conjugated anti-IgG as described in Example 1. The results of these treatments are presented in Table 3, and graphically displayed in FIG. 3.

TABLE 3
ADSORPTION OF IMMUNE COMPLEXES FROM SERUM BY POLYSTYRENE PLATES COATED WITH GAMMA-GLOBULINS FROM VARIED SPECIES

| Coating Source | Normal | Rheumatoid Arthritis | Remission Lupus |
|---|---|---|---|
| Goat | 0.102 | 0.831 | 0.108 |
| Dog | 0.052 | 0.483 | 0.136 |
| Horse | 0.001 | 1.040 | 0.001 |
| Rabbit | 0.068 | 1.045 | 0.178 |

TABLE 3-continued

ADSORPTION OF IMMUNE COMPLEXES FROM SERUM BY POLYSTYRENE PLATES COATED WITH GAMMA-GLOBULINS FROM VARIED SPECIES

| Coating Source | Normal | Rheumatoid Arthritis | Remission Lupus |
| --- | --- | --- | --- |
| Sheep | 0.131 | 1.024 | 0.154 |

Legend:
The numbers listed in Table 3 refer to the MEAN OPTICAL DENSITY (MEAN ADSORBANCE) at 490 nm obtained following the treatment listed above for plates coated with gammaglobulin fractions derived from the species listed on the left edge of the table.
Serum sources are listed along the top edge of the table.
Abbreviations:
SLE: Systemic Lupus Erythematosus
RA: Rheumatoid Arthritis The gammaglobulin-mediates ability of coated supports to specifically affix immune complexes is illustrated by comparison of Table 3 with Table 1. Each of the coating groups was able to affix immune complexes from certified human sera appropriate to the pathological status of the human source. Hence, all gammaglobulin coatings tried confered selectivity for immune complex absorption, although different qualities may be observed for different coatings. The same procedure should work equally well for whole blood or anticoagulated plasma.

EXAMPLE 4

Removal of Immune Complexes by Coated Polystyrene Beads

Figure 4:
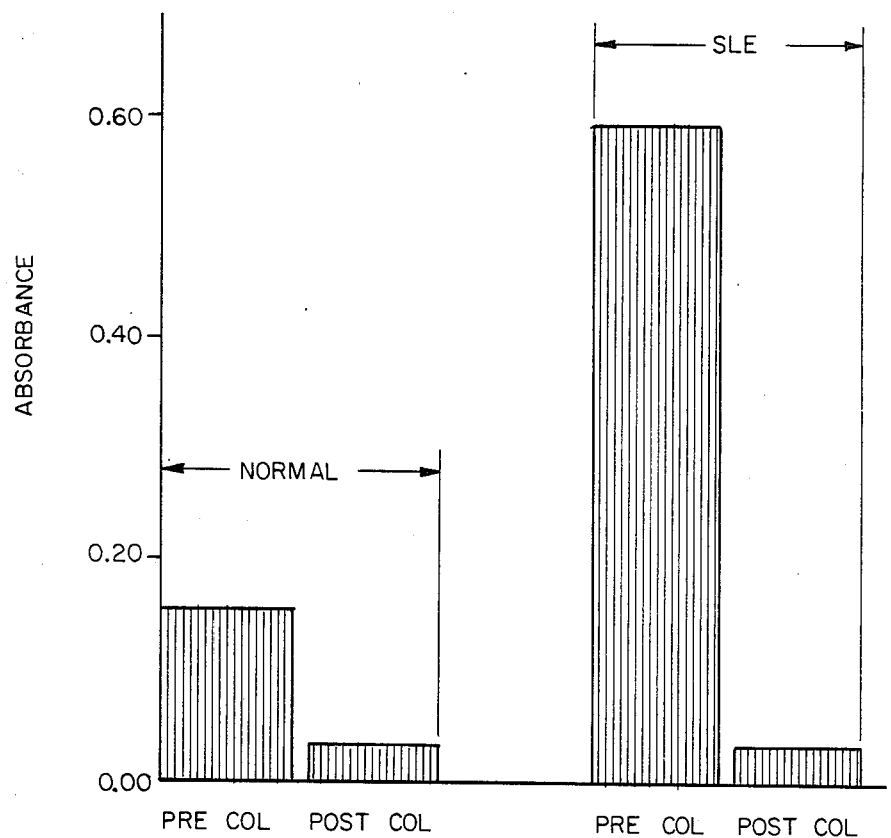
FIG. 4 is a bar graph of immunoassay results on sera before and after adsorption of the immune complexes in a column that has been pretreated with immunologically non-specific glycoproteins.

An alkaline preparation of bovine gammaglobulins (1 mg bovine gammaglobulins/ml in pH 9.6 carbonate buffer, as in Example 1) was used to treat polystyrene beads (BioBeads, SM4, 20–50 mesh, BioRad Laboratories, Richmond, Calif.) for the purpose of adhering immune complexes to the beads. Serum containing immune complexes, previously assayed as to their immune complex level as in Example 1, was passed through a column of said beads maintained at 37° C., and the quantity of immune complexes determined both before and after column filtration. The results of this procedure are presented in Table 4, and are displayed graphically in FIG. 4.

TABLE 4

REMOVAL OF IMMUNE COMPLEXES FROM SERUM BY COATED POLYSTYRENE BEADS

| Serum Source | Pre-Column OD | Post-Column OD |
| --- | --- | --- |
| Normal | 0.155 | 0.033 |
| Severe SLE | 0.601 | 0.035 |

Legend:
Separately, serum samples from undiseased and from known systemic lupus erythematosus afflicted individuals were passed over a column treated with alkaline bovine gammaglobulins as previously described.
Immune complex assays were performed before and after treatment (pre- and post-column).
The optical densities exhibited by the samples before and after treatment are listed in the table.
Abbreviation:
SLE: Systemic Lupus Erythematosus Polystyrene beads coated with bovine gammaglobulins in this manner selectively and expeditiously absorbed immune complexes. Approximately 90% of the complexes were removed by one passage through the column. Alkaline gammaglobulin treatment of polystyrene beads is thus effective in relatively quickly removing these agents from serum samples. Therefore, a sufficiently large column prepared with similar glycoproteins should remove significant amounts of immune complexes when whole blood is passed through the column at through-put rates that can enable the present invention to be used in therapeutic treatment methods. Serum treatment in this manner will facilitate selective removal of circulating immune complexes present. Furthermore, column isolation of immune complexes from large quantities of blood will provide for concentration of said complexes, allowing for detection of minor components such as immunoglobulin ideotypes, rare subclasses of antibodies, and rare or sequestered antigens as might be present in said complexes. The same procedure should work equally well for anticoagulated plasma.

EXAMPLE 5

The purpose of this example is to illustrate the beneficial effect of liquid-phase bovine gammaglobulin on immune complex assays performed on immobilized glycoprotein coats. This addition proved highly effective at reducing baseline values for this normal serum sample containing low levels of immune complexes. For this example, two serum samples were tested. The first of these samples was derived from an individual exhibiting no apparent clinical pathology, but still reacting positive in the immune complex assay previously described. The second serum sample was obtained from an individual having a severe case of systemic lupus erythematosus. These two serum samples were diluted with 0.15M NaCl containing 0.01M potassium phosphate pH 7.4 (phosphate buffered saline), or with phosphate buffered saline containing bovine gammaglobulin at a concentration of 1 mg bovine gammaglobulin per ml of buffer.

After diluting the samples, each of the four preparations was tested for immune complexes according to the solid-phase assay previously described with particularity in Examples 1 through 3. The chestnut-brown color arising from the enzyme-linked portion of the assay was read at 490 nm on a Dynatech MR600 plate reader, and the results both listed in the accompanying table and plotted on the bar graph.

TABLE 5

| Diluent | BGG Absent | BGG Present |
| --- | --- | --- |
| Serum Source | | |
| Normal | 0.739 | 0.020 |
| SLE | 0.390 | 0.323 |

Legend: Serum derived from clotted blood was used for the tests in the table above. The designation "Normal" is herein used to denote serum derived from an individual showing no clinically apparent manifestation of disease at the time of phlebotomy. The designation "SLE" is used in this example to denote serum derived from an individual clinically diagnosed as suffering from systemic lupus erythematosus. Prior to assay, 1 part serum was diluted with 15 parts of diluting agent. For the "BGG Absent" column, the diluting agent used in this example was 0.15 M NaCl buffered to a pH of 7.4 with 0.01 M potassium phosphate. For the "BGG Present" column, bovine gammaglobulin was dissolved in phosphate buffered saline (previously defined) to the extent of 0.5 mg bovine gammaglobulin per ml of phosphate buffered saline.

The diluted sera were subjected to the immune complex assay described in Examples 1 through 3. The numbers presented in the table represent the mean absorbance for four replicate determinations.

Figure 5:
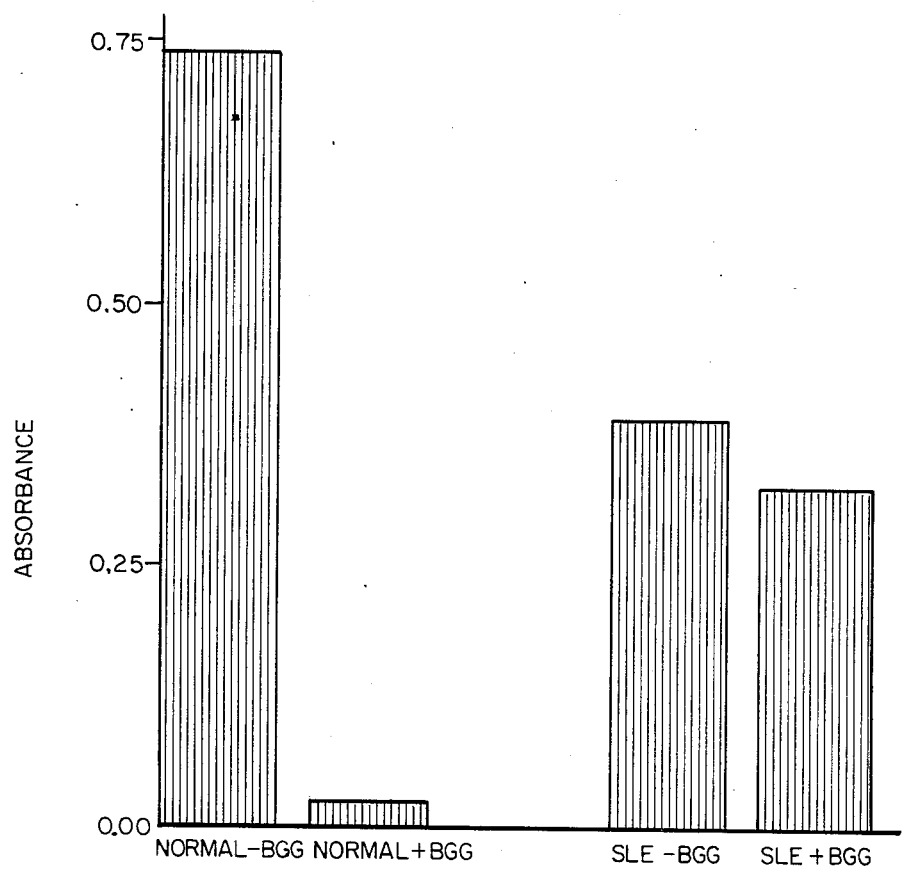
FIG. 5 is a bar graph of the results of another embodiment of the present invention.

In FIG. 5 the results of serum samples diluted either with phosphate buffered saline or with phosphate buffered saline containing 1 mg bovine gammaglobulin per ml are shown. After dilution, the samples were assayed for immune complexes using the solid-phase assay described in Examples 1, 2 and 3. The height of the bar on FIG. 5 represents the mean absorbance found after 4 replicate assays. In FIG. 5, normal refers to serum obtained from an individual presenting no apparent clinical pathology. SLE refers to serum obtained from an individual suffering from severe systemic lupus erythematosus. −BGG refers to serum diluted in phosphate buffered saline alone while +BGG refers to serum diluted in phosphate buffered saline containing 1 mg bovine gammaglobulin per ml.

The addition of bovine gammaglobulin to the serum diluent reduced the absorbance found in the normal serum sample nearly forty-fold. Indeed, very little color was observable when the assay was performed on bovine gammaglobulin diluted normal serum. Conversely, dilution of serum obtained from an individual with an authentic autoimmune disorder with bovine gammaglobulin-containing buffer produced very little change in color, either visually or as detected by the spectrophotometric device. Accordingly, a 16 fold difference between normal and autoimmune state serum was noted after dilution by bovine gammaglobulin-containing buffer whereas no differentiation existed without such addition. In additional similar assay trials, this procedure virtually eliminates false positives for individuals without apparent pathology while individuals with significant disease remain elevated. These results clearly indicate the beneficial effect of inclusion of proteins like bovine gammaglobulin in the diluting agent, such effect being effective to eliminate the false positive rate without materially altering the true positive rate.

EXAMPLE 6

The foregoing examples illustrate the utility of the immune complex affixation method described in this patent. The data presented in this example demonstrates that the fixation techniques described heretofore are also applicable to plasma and whole blood, regardless of which common anticoagulant is used.

For this example, blood was collected from a healthy donor and from an individual with rheumatoid arthritis. Four tubes were drawn from each donor. The first tube contained no anticoagulants. The three remaining tubes contained anticoagulants. The second tube contained sufficient ethylene diamine tetraacetate (EDTA) to make the final concentration 1.5 mg EDTA/ml blood; the third tube contained sufficient heparin to make the final concentration 28 USP units heparin/ml blood; the fourth tube contained sufficient sodium citrate to make the final concentration 3.5 mg sodium citrate/ml blood.

The specimens were prepared and assayed as follows:

The first pair of specimens (one each from normal and CIC elevated subjects) were allowed to clot normally, and the sera collected. These sera were subjected to the immune complex assay procedures described in Examples 1 and 5.

An aliquot of whole blood was removed from each of the second pair of specimens, anticoagulated with ETDA, and subjected to the immune complex assay described in Examples 1 and 5. The plasma components of each specimen were separated by centrifugation, and the plasma samples assayed for immune complexes as described in Examples 1 and 5.

An aliquot of whole blood was removed from each of the third pair of specimens, anticoagulated with heparin, and assayed as above. The plasma of each pair of specimens were separated by centrifugation and assayed as above.

An aliquot of whole blood was removed from each of the fourth pair of specimens, anticoagulated with sodium citrate, and assayed as above. The plasma components of each specimen were separated by centrifugation and assayed as above.

Figure 6:
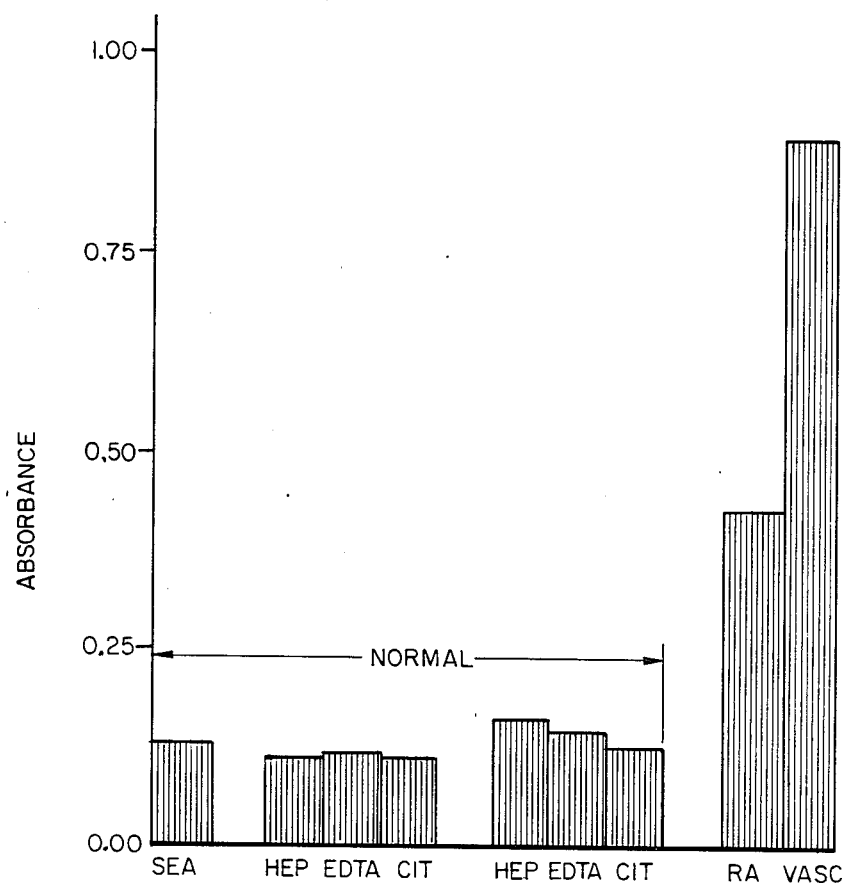
FIG. 6 is a bar graph of the results of using the present invention with whole blood.

The results of these investigations is listed in Table 6, and illustrated graphically in FIG. 6.

Referring to Table 6, it is clear that the addition of anticoagulant to whole blood for the purpose of preventing clot formation is without deleterious effect upon the ability of the assay to discriminate specimens containing normal and elevated amounts of immune complexes. In general, addition of anticoagulants appeared to improve the assay performance slightly, as is evidenced by the higher fold elevation values observed for anticoagulated vs plasma samples. This finding fundamentally rules out mechanisms of immune complex adherance based upon components of serum such as complement or conglutinin. Such agents require calcium ions for activity, and the addition of either EDTA or citrate removes free calcium from blood. As a consequence, it may be concluded that this example both illustrates the utility of the thin glycoprotein film method of immune complex affixation, and highlights the surprising properties of such thin glycoprotein films as used in the assay.

Serum samples from individuals exhibiting immune complex disorders are significantly elevated compared to those from normal individuals, whether the blood from these individuals has been inhibited from clotting or not, and without regard to the anticoagulant used. Because of this behavior, the procedure described for the affixation of immune complexes may be used with plasma or whole blood samples for the assay or for removal of such complexes as might be present in them according to the procedures described. It is apparent from the foregoing tests that there is no reason to believe that the method for removing immune complexes described herein is restricted to those found in serum, plasma, or blood. It is apparent that immune complexes present in diverse sources such as urine, ascites fluid, cerebrospinal fluid, or from in vitro mixtures performed in the laboratory will be capable of being affixed to the glycoprotein coating described herein, thereby greatly enhancing the utility of the invention described herein. Indeed, as is shown in Example 7, the principle of immune complex removal from anticoagulated whole blood and/or plasma by passage through a column prepared from glycoprotein-coated beads also applies to the therapeutic apheretic removal of immune complexes from patients afflicted with autoimmune disorders.

TABLE 6

| | Immune Complex Assay of Specimens Derived From Whole Blood | | | |
|---|---|---|---|---|
| CONDITION | ABSORBANCE | CORRECTION | FINAL ABSORBANCE | FOLD ELEVATION |
| NORMAL | | | | |
| Serum | 0.128 | 1.00 | 0.128 | 1 |
| Plasma-hep | 0.107 | 1.00 | 0.107 | 1 |

TABLE 6-continued

| | | | | |
|---|---|---|---|---|
| Plasma-EDTA | 0.118 | 1.00 | 0.118 | 1 |
| Plasma-cit | 0.099 | 1.11 | 0.110 | 1 |
| Whole blood-hep | 0.107 | 1.49 | 0.159 | 1 |
| Whole blood-EDTA | 0.095 | 1.49 | 0.142 | 1 |
| Whole blood-cit | 0.075 | 1.66 | 0.124 | 1 |
| CIC ELEVATED | | | | |
| RA Plasma | 0.765 | 1.00 | 0.765 | 6 |
| Plasma-hep | 0.864 | 1.00 | 0.864 | 8 |
| Plasma-EDTA | 1.031 | 1.00 | 1.031 | 9 |
| Plasma-cit | 0.830 | 1.11 | 0.921 | 8 |
| Whole blood-hep | 0.637 | 1.80 | 1.145 | 7 |
| Whole blood-EDTA | 0.733 | 1.80 | 1.318 | 9 |
| Whole blood-cit | 0.579 | 2.12 | 1.227 | 10 |

LEGEND: Samples were obtained either from an individual free from clinically apparent pathology (Normal) or from individuals with rheumatoid arthritis (RA) or vasculitis. Serum refers to serous specimens obtained after centrifuging clotted blood. Plasma refers to the supernatant obtained after centrifuging whole blood containing an anticoagulant. Anticoagulants are abbreviated as follows: hep, heparin; EDTA, ethylene diamine tetraacetate; cit, citrate. When noted in the table, anticoagulated whole blood was tested. Factors refer to volume corrections necessary because of added volume (citrate) or cell volume in whole blood. Citrate solutions comprised 10% of the final volume. Hematocrits were taken as 34% of blood volume for normals and 44% for CIC elevated samples. Fold elevation refers to the absorbance in any given CIC-elevated specimen divided by that found for its respective normal.
Four specimens of blood were withdrawn from each individual, one in a tube devoid of anticoagulants, and three separately containing different anticoagulants. The following abbreviations refer to the anticoagulant contained in specimens thus obtained: (1) hep — heparin, 28 IU/ml; (2) EDTA — ethylene diamine tetraacetate, 1.5 mg/ml; (3) cit — sodium citrate, 3.5 mg/ml. Whole blood, plasma or serum (SER) derived from the specimens were subjected to the assay described fully in Examples 1 and 5. In the figure, the height of the bar represents the absorbance measured following the assay procedure. The data from this table is shown graphically in FIG. 6.

EXAMPLE 7

As indicated in Example 3, columns prepared from glycoprotein coated solid supports exhibit the capacity of extracting immune complexes from serum samples. Further utility of such columns is afforded by the data presented in the present example. Samples of bodily fluids such as blood are often prohibited from clotting through the addition of anticoagulation agents such as heparin, ethylene diamine tetraacetate (EDTA) or salts of citric acid. Such compounds inhibit clotting either by interfering with the proteolytic steps leading to fibrin activation (heparin), or by chelating calcium (EDTA or citrate). In this example, it is shown that such agents as heparin, EDTA, or citrate are without effect upon the ability of glycoprotein coated solid supports to adsorb or affix immune complexes regardless whether the sample passed through the column was whole blood or plasma derived therefrom. Furthermore, immune complex fixation in the presence of these anticoagulants was at least as equal to that for serum, devoid of anticoagulants. The concentrations of anticoagulants tested for this example were higher than those normally used for apheretic purposes in human beings. Because these high concentrations of anticoagulants exhibited no deleterious effects on immune complex adsorption, it is obvious that the intermediate anticoagulant concentrations used for apheretic applications will similarly be without deleterious effects upon the immunoadsorption of complexes.

For the purpose of this example, blood specimens from an individual afflicted with rheumatoid arthritis were drawn into tubes containing either heparin, EDTA, or sodium citrate. A control specimen was also drawn into a tube containing no anticoagulant. The control specimen was allowed to clot and the seru reserved. Immune complex assays were performed as described in Example 1, except that the incubation for immune complex detection (second incubation) was performed with horseradish peroxidase-conjugated goat antiserum directed against immune classes IgG, -M, and -A were used in place of the IgG specific antibodies used in Example 1. Use of such multivalent antibodies as these (IgG, -M and -A specific) further enhances the chemical sensitivity of the test, thereby improving the general applicability of the adsorption method presented herein.

Following the immune complex assay, 0.25 ml aliquots of undiluted samples were added to columns prepared from BGG coated polystyrene beads as described for Example 3. The columns were incubated at 37° for 30 minutes, as before. Then the sample was eluted as a bolus, therefore was not appreciably diluted. Additional phosphate buffered saline was passed through the column to make the final dilution 1:16 and to chase any loosely bound immune complexes off the column. The resulting diluted eluate was subsequently assayed for immune complexes without additional dilution. An additional control was also prepared in which serum was incubated in contact with untreated polystyrene beads. The eluate of that column was also assayed as above.

The percent of immune complexes removed by the procedure was calculated as follows:

$$\% \text{ Removal} = \frac{OD_{init} - OD_{final}}{OD_{init}} \times 100$$

Figure 7:
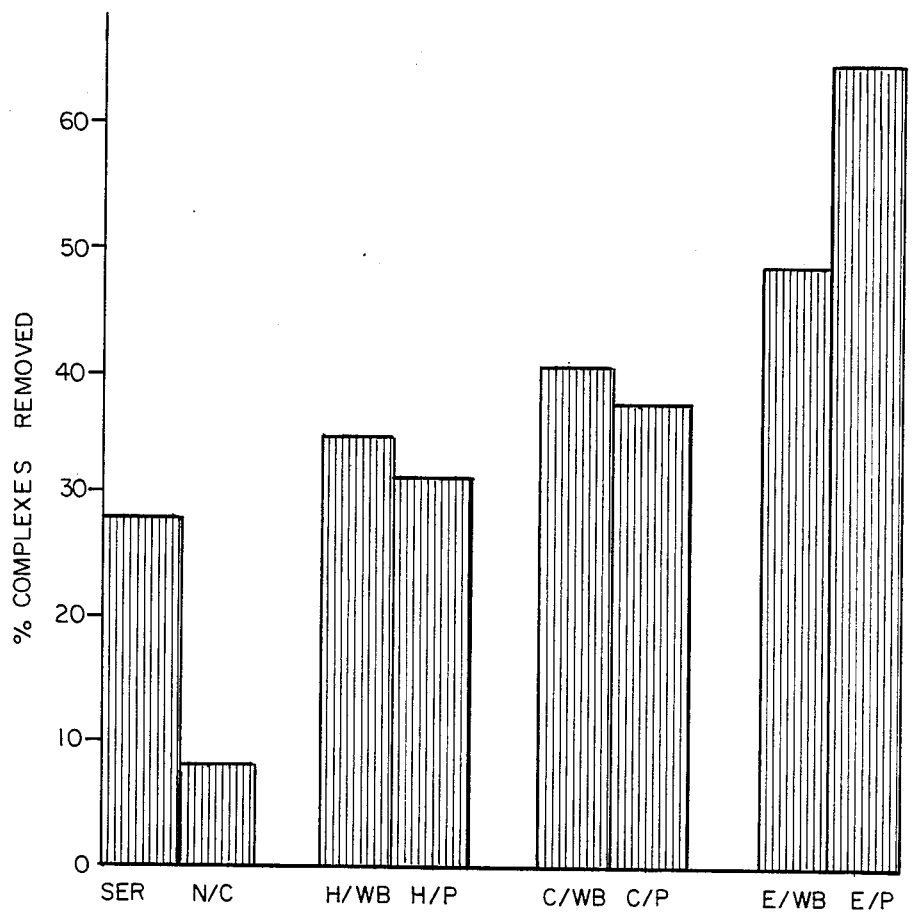
FIG. 7 is a bar graph of the results of using the present invention with whole blood using columns of glycoprotein-coated polystyrene beads.

The results of this procedure are presented in Table 7 and are graphically illustrated in FIG. 7.

Referring to both Table 7 and FIG. 7 it is clearly apparent that the presence of anticoagulants is without deleterious effect upon the ability of glycoprotein treated supports to remove immune complexes from either plasma or whole blood. This is expected since calcium is not required for the glycoprotein-immune complex interaction which fixes the complexes to the support as taught in the previous examples. Uncoated polystyrene support materials were unable to affix significant amounts of immune complex, again in agreement with the principles taught in Examples 1-3.

As is demonstrated by the teaching in this example, glycoprotein films applied to suitable supporting materials will be highly useful for the purpose of removing immune complexes from whole blood or from plasma, regardless of the anticoagulant which may be present. This attribute makes it possible to adsorb immune complexes from the blood for therapeutic treatment of any immune-complex associated disease or disorder. It also adds to the utility of the procedure since the column can serve to concentrate certain rare antibody or antigen types present in the immune complexes. Following elution of said concentrated complexes from such columns, detection of rare antigens or antibodies can be performed with great facility using the assay method taught in Examples 1 and 5.

TABLE 7

| COLUMN LOADED WITH: | % COMPLEXES REMOVED |
| --- | --- |
| Serum | 28% |
| Serum* | 8% |
| Heparin-treated whole blood | 34% |
| Heparin-treated plasma | 31% |
| Citrate-treated whole blood | 40% |
| Citrate-treated plasma | 37% |
| EDTA-treated whole blood | 48% |
| EDTA-treated plasma | 64% |

*Serum passaged through non-coated polystyrene columns
LEGEND: Removal of Immune Complexes from Serum, Plasma, and Whole Blood using Columns of Glycoprotein-coated Polystyrene Beads.
Blood was drawn into separate vacutainer tubes, each containing a different anticoagulant. The tubes were designated as follows:
Heparin, final blood concentration of 28 USP units/ml.
Citrate, final blood concentration of sodium citrate of 3.5 mg/ml.
EDTA, final blood concentration of sodium EDTA of 1.5 mg/ml.
After collection, an aliquot of each blood specimen was subjected to centrifugation and the plasma withdrawn. These plasma samples were used whenever indicated in the Table. Whole blood refers to the anticoagulated specimen prior to centrifugation. Serum refers to a blood specimen which was drawn into a tube and allowed to clot prior to separation of the fluidic component.
For the column extraction of immune complexes, 0.25 ml aliquots of each sample noted in the Table were added to each of 8 columns and allowed to incubate for 30 minutes at 37° C. The remaining serum components were eluted from the columns with 3.75 ml PBS and the eluate assayed for immune complexes. The percentage of complexes removed was calculated as noted in the accompanying text.
For the purposes of comparison, serum controls were also passed through columns prepared with thin glycoprotein films on polystyrene supports. Serum refers to a blood specimen which was drawn into a tube and allowed to clot prior to separation of the fluidic component. Such serum controls were devoid of anticoagulants. The purpose of such TABLE 7-continued serum controls was to demonstrate that, regardless of how high or low the anticoagulant concentration, there was no deleterious effect of said anticoagulants on the ability of glycoprotein-coated substrates to remove immune complexes from fluids for either the purposes of assay or of immune complex immunoadsorption from blood or plasma for the purpose of therapeutic apheretic applications.
For the column extraction of immune complexes, 0.25 ml aliquots of each sample noted in the Table were added to each of 8 columns and allowed to incubate for 30 minutes at 37° C. The remaining serum components were eluted from the columns with 3.75 ml PBS and the eluate assayed for immune complexes. The percentage of complexes removed was calculated as noted in the accompanying text.
In FIG. 7, the specimen added to the column is indicated below the bar. The height of the bar represents the percentage of immune complexes removed from the specimen. Abbreviations used are as follows:

SER: Serum
N/C: Serum passaged over a column of non-coated polystyrene.
H/WB: Heparin treated whole blood.
H/P: Plasma derived from heparin treated whole blood.
C/WB: Citrate treated whole blood.
C/P: Plasma derived from citrate treated whole blood.
E/WB: EDTA treated whole blood.
E/P: Plasma derived from EDTA treated whole blood.

The foregoing examples serve to illustrate the efficacy and utility of thin glycoprotein films to affix immune complexes to solid supports. While the illustrating examples have shown that the antibody molecules present in the complexes may readily be determined, there is no reason to limit the detection method to the antibody classes or subclasses contained therein. Further utility of the method is afforded through the use of antigen specific detection means whereby the disease state may be ascertained. The following descriptions illustrate means whereby such detection may be performed.

Antigen and antibody components in immune complexes possess unoccupied binding sites which can be detected through specific interaction with labelled or conjugated materials. As a consequence, immune complex fixation as described in Examples 1, 3, and 4 followed by incubation with an enzyme conjugated antigen will lead to subsequent fixation of the conjugated antigen. This property will lead to antigen-specific enzyme-catalyzed reaction if the antibodies directed against the antigen are present in the complex. As a consequence, the enzyme immunoassay will be positive if the complex contains antibodies directed against the antigenic substance, while the enzyme immunoassay will be negative if these components are absent. This method affords additional utility by permitting disease-specific inquiry as to the precise antibody composition of the complex. Conjugation need not be limited to enzymes. Addition of fluorescent chemicals such as fluorescence or the like to the antigen will impart fluorescence to the complex if said antibody substances are present; similarly, conjugation of the antigen with a radionuclide will impart radioactivity to the complex provided said antibody substances are present in the previously affixed complex. Many other methods of detection also exist, and each of these methods will yield positive indications provided that the antibody component exists in the complex affixed according to the methods described herein.

Likewise, the presence of the precise antigens in the complex, as described herein will also permit the detection of such antigens using conjugated antibodies directed against that antigen. As a consequence, if one incubates enzyme-conjugated antibodies with an immobilized immune complex prepared according to the methods described herein, the enzyme-catalyzed reaction will indicate the presence of said antigens in the complex. Conjugation again need not be limited to enzymes. Addition of fluorescent chemicals such as fluorescence or the like to the antibody will impart fluorescence to the complex if said antigenic substances are present. Similarly, conjugation of the antibody with a radionuclide will impart radioactivity to the complex provided said antigenic substances are present in the previously affixed complex. As with the detection of antibodies described many other methods of detection for the antigens also exist, and each of these methods will yield positive indications provided that the antigenic component exists in the complex affixed according to the methods described herein.

The described technology for coating supports with immunologically non-specific peptide linked amino acids including oligopeptides, modified oligopeptides, polypeptides, modified polypeptides, proteins, and modified proteins, which have the ability to directly and selectively affix immune complexes by absorption, adsorption or other mechanisms of attachment, has broad utility in either assaying bodily fluids for the presence of circulating immune complexes and for removing circulating immune complexes. In particular, glycosylation of any of the foregoing immunologically non-specific peptide linked amino acid based classifications should produce the most useful compositions for isolation and identification of immune complexes. The ease of use and widespread applicability of this technology will be readily appreciated by one skilled in the art, after thorough appreciation of the method is attained. The treatment of solid supports in this manner affords many important and useful approaches to the detection and treatment of autoimmune diseases, suggesting a wide variety of new procedures. Such procedures can include, but are not limited to, detection of the antibody class and subclass composition of the immune complex, determination of the antigen nature of the immune complex, and removal of such complexes as may be present in serum, other bodily fluid, or fluid of any source, whether corporeal or extracorporeal. The techniques described herein therefore, have widespread applicability and broad utility for directly detecting circulating immune complexes in serum and for directly removing circulating immune complexes from serum.

Without being bound to any specific theory, it is contemplated that varying degrees of glycosylation or other similar, functionally equivalent substituents to immunologically naive species of the described oligopeptides, polypeptides and proteins will produce a family of materials having the capability of directly attaching immune complexes present in serum for the purpose of detection and removal.

It is contemplated that the inventive concepts herein described may be variously otherwise embodied and it is intended that the appended claims be construed to include alternative embodiments of the invention except insofar as limited by the prior art.

What is claimed is:

1. A method of removing immune complexes from a serum comprising the steps of:
    (1) fixing a composition to a substrate under conditions preselected to facilitate the fixation of such composition to said substrate to form a coating thereof said composition containing an alkaline treated gammaglobulin derived from animals not immunized against any antigenic determinant;
    (2) contacting said coating on said substrate with specific sera containing immune complexes in a manner to facilitate adherence of the immune complexes contained in the sera to the Fc portion of the gammaglobulin in said coating;
    whereby immune complexes present in said sera are bonded to said coating on said substrate.

2. A solid article for selectively removing immune complexes from solutions placed in contact with such article, comprising:
    support means adapted to be contacted with solutions containing immune complexes; and
    coating means comprising a composition containing an alkaline treated gammaglobulin derived from animals not immunized against any antigenic determinant and capable of being affixed to said support means to form a coating thereon, such coating further being capable of adhering immune complexes present in specific fluids to the Fc portion of the said selected gammaglobulin present in said coating when such fluids are placed in contact with said coating,
    whereby immune complexes present in such fluids are selectively attached to said coating means.

3. A method of performing an assay for immune complexes from at least one serum comprising the steps of:
    contacting a support with a solution containing an alkaline treated gammaglobulin derived from animals not immunized against any antigenic determinant;
    fixing the selected gammaglobulin to the support to form a coating thereon;
    removing any excess solution from the support,
    contacting the coating with a fluid to be tested for the presence of immune complexes,
    facilitating adherence of the immune complexes present in said fluid to the Fc portion of the said selected gammaglobulin present in said coating, and
    detecting the immune complexes retained by said coating.

4. An article for selectively removing immune complexes from fluids containing immune complexes that are contacted with such article, comprising:
    support means adapted to be contacted with fluids containing immune complexes; and
    coating means comprising a composition containing an alkaline treated gammaglobulin derived from animals not immunized against any antigenic determinant affixed to said support means in the form of a coating such coating means being affixed to said support means by incubation at a preselected temperature for a sufficient period of time to facilitate such fixation whereby the affixed coating is capable of removing immune complexes present in specific fluids when such fluids are placed in contact with said coating means;
    whereby immune complexes present in such fluids are selectively attached to the Fc portion of the said selected gammaglobulin present in said coating.

5. A method of treating a support substrate to provide the support with the capability of directly and selectively affixing immune complexes to such prepared substrate, comprising the steps of:
    providing a substrate capable of containing on the surface thereof a preselected coating;

contacting said substrate with a composition containing an alkaline treated gammaglobulin derived from animals not immunized against any antigenic determinant which is capable of being attached to said substrate to form a coating which is capable of adhering to the Fc portions thereof immune complexes present in compositions that are placed in contact with said coating in a manner that permits subsequent detection and identification of the presence of said immune complexes.

6. A method of treating a substrate to provide the substrate with the capability of directly and selectively affixing immune complexes to such prepared substrate comprising the steps of:

providing a substrate capable of containing on the surface thereof a preselected coating;

contacting said substrate with solution having an alkaline pH and including a composition comprising an alkaline treated gammaglobulin derived from animals not immunized against any antigenic determinant which combustion when incubated at a preselected temperature for a sufficient period of time is capable of being attached to said substrate to form a coating, which coating is capable of adhering immune complexes present in compositions that are placed in contact with said coating and affixed thereto so as to permit subsequent identification of the presence of said immune complexes.

* * * * *